(12) United States Patent
O'Connor

(10) Patent No.: US 6,991,898 B2
(45) Date of Patent: Jan. 31, 2006

(54) DIAGNOSTIC TEST DEVICE AND METHOD OF USING SAME

(75) Inventor: Amanda Lee O'Connor, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 93 days.

(21) Appl. No.: 10/689,414

(22) Filed: Oct. 20, 2003

(65) Prior Publication Data

US 2005/0084842 A1 Apr. 21, 2005

(51) Int. Cl.
*C12Q 1/00* (2006.01)

(52) U.S. Cl. ............... 435/4; 435/30; 435/287.7; 435/287.9; 435/288.2; 435/288.7; 435/309.1; 435/808; 435/970

(58) Field of Classification Search ............... 422/58; 435/287.3, 287, 288.1, 288.2, 288.7, 309.1, 435/808, 970, 4, 30, 287.9; 600/572
See application file for complete search history.

(56) References Cited

U.S. PATENT DOCUMENTS

| | | | |
|---|---|---|---|
| 3,004,681 A | 10/1961 | Jinkens et al. | 215/227 |
| 3,163,160 A | 12/1964 | Cohen | 600/572 |
| 3,450,129 A | 6/1969 | Avery et al. | 600/572 |
| 3,634,038 A | 1/1972 | Rampy | 422/56 |
| 3,640,268 A | 2/1972 | Davis | 600/572 |
| 3,776,220 A | 12/1973 | Monaghan | 600/572 |
| 3,890,954 A | 6/1975 | Greenspan | 600/572 |
| 3,918,435 A | 11/1975 | Beall et al. | 600/572 |
| 3,923,604 A | 12/1975 | Monaghan | 600/572 |
| 3,954,563 A | 5/1976 | Mennen | 600/572 |
| 3,954,564 A | 5/1976 | Mennen | 600/572 |
| 4,014,746 A | 3/1977 | Greenspan | 435/243 |
| 4,184,483 A | 1/1980 | Greenspan | 600/572 |
| 4,196,167 A | 4/1980 | Olsen | 422/61 |
| 4,312,950 A | 1/1982 | Snyder et al. | 600/572 |
| 4,340,670 A | 7/1982 | Mennen | 435/25 |
| 4,353,868 A | 10/1982 | Joslin et al. | 422/101 |
| 4,355,113 A | 10/1982 | Mennen | 435/287.6 |
| 4,586,604 A | 5/1986 | Alter | 206/210 |
| 4,700,694 A | 10/1987 | Shishido | 600/104 |
| 4,707,450 A | 11/1987 | Nason | 600/572 |
| 4,748,113 A | 5/1988 | Marshall | 435/12 |
| 4,749,655 A | 6/1988 | Monthony et al. | 600/572 |
| 4,770,853 A | 9/1988 | Bernstein | 422/58 |
| 4,813,432 A | 3/1989 | Saint-Amand | 600/562 |
| 4,830,010 A | 5/1989 | Marshall | 600/300 |
| 4,978,504 A | 12/1990 | Nason | 422/61 |
| 5,078,968 A | 1/1992 | Nason | 422/58 |
| 5,146,928 A | 9/1992 | Esser | 600/569 |
| 5,238,649 A | 8/1993 | Nason | 422/58 |
| 5,256,537 A | 10/1993 | Phillips et al. | 435/7.1 |

(Continued)

FOREIGN PATENT DOCUMENTS

| | | |
|---|---|---|
| EP | 0 277 009 | 8/1988 |
| EP | 0 306 336 | 3/1989 |
| EP | 0 357 261 | 3/1990 |
| EP | 0 357 892 | 3/1990 |
| GB | 2 072 513 | 10/1981 |
| WO | WO 95/11672 | 5/1995 |

*Primary Examiner*—David A. Redding
(74) *Attorney, Agent, or Firm*—Steven D. Flack; Richard M. Shane

(57) ABSTRACT

A self contained diagnostic test device is provided for use in the collection and detection of a biological specimen or the like. The device comprises a tubular swab and reagent dispensing cap component for receiving specimens. The reagent dispensing cap component includes barrel, reagent chamber, and results window subcomponents, and delivers one or more selected reagents to a specimen testing chamber for contacting the collected specimen, upon the rotation of the reagent chamber component.

25 Claims, 7 Drawing Sheets

U.S. PATENT DOCUMENTS

| | | | |
|---|---|---|---|
| 5,266,266 A | 11/1993 | Nason | 422/58 |
| 5,425,377 A | 6/1995 | Caillouette | 600/572 |
| 5,427,739 A | 6/1995 | Meserol et al. | |
| 5,766,962 A | 6/1998 | Childs et al. | 436/518 |
| 5,869,003 A | 2/1999 | Nason | 422/58 |
| 5,879,635 A | 3/1999 | Nason | 422/102 |
| 6,010,462 A | 1/2000 | Stoermer, III | 600/572 |
| 6,248,294 B1 | 6/2001 | Nason | 422/58 |
| 6,277,646 B1 * | 8/2001 | Guirguis et al. | 436/165 |
| 6,517,809 B1 | 2/2003 | Marshall | 424/1.37 |
| 6,524,530 B1 | 2/2003 | Igarashi et al. | 422/58 |

* cited by examiner

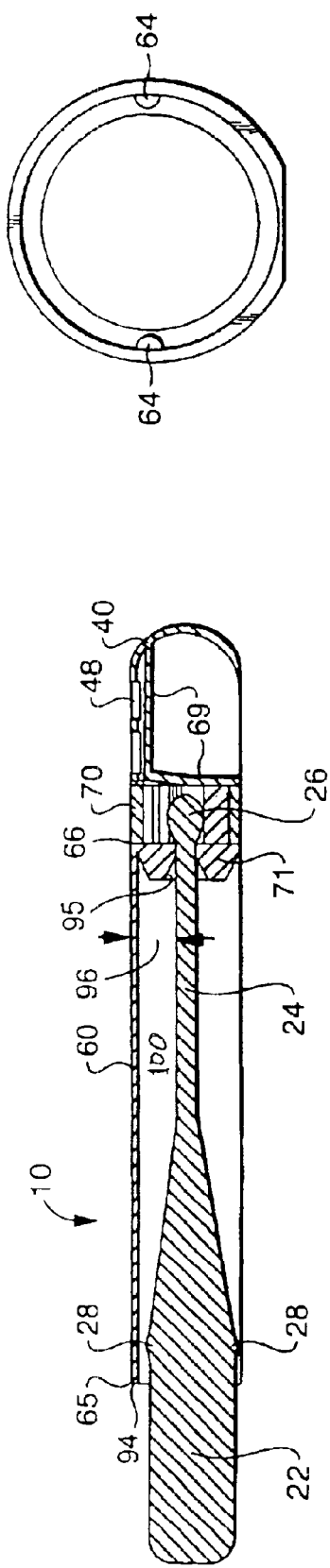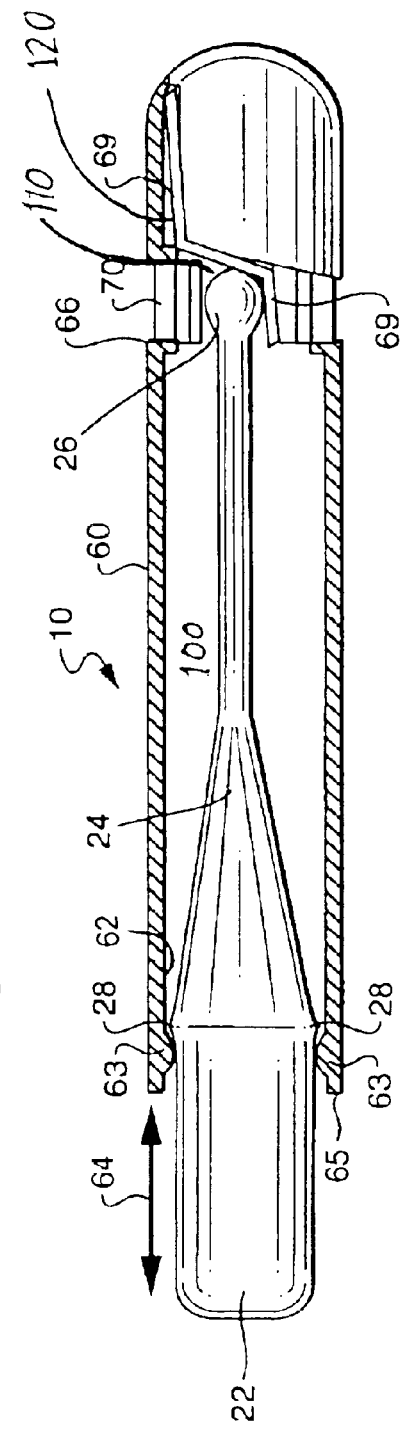

DIAGNOSTIC TEST DEVICE AND METHOD OF USING SAME

FIELD OF THE INVENTION

The present invention relates to diagnostic test devices and methods of using the same. More particularly, the present invention relates to diagnostic test devices used for detecting microorganisms in a body cavity, interior body space or an environmental setting.

BACKGROUND OF THE INVENTION

Medical swabs are generally known in the art for use in collecting biological specimens from a patient for further analysis. Such medical swabs commonly comprise a fibrous swab tip at one end of an elongated stick or shaft, which is manipulated to contact the swab tip with selected tissue cells, secretions, fluids or other biological specimens obtained, for example, from within the ear, nose, throat, vaginal opening or other body cavity/opening of a patient. As a result, some of the targeted biological specimen adheres to the swab tip. The swab tip then can be contacted with one or more chemical reagents to indicate the presence of infection or other information regarding patient condition. Such reagent testing may either be quantitative in character, in that it produces a quantifiable result, qualitative (as providing matter of degree of infection or contamination by using a scale system), or a positive/negative-type test result, in that it indicates the presence of a particular condition, but does not provide details as to degree.

Alternatively, such swab testing may be used as part of environmental condition monitoring. For instance, such swabbing may be done in a food service area to determine the presence or absence of environmental or food pathogens or contaminants.

Such medical swabs may be either used as part of a storage/transport unit for transporting a biological sample to a laboratory for further analysis, or alternatively, as part of a portable test detection device, designed to provide an immediate or relatively quick indication of a patient's or environmental condition at the time of the test. If the swab is part of a storage/transport unit, it is likely that such unit will include growth media or other chemistries to aid in maintaining the specimen in a viable state during transport.

Tests commonly performed with such patient specimens include, by way of example, fluorescent tests, enzymatic tests, monoclonal based tests, agglutination tests, and others. Moreover, swabs and similar reagent test methods are also used in a variety of nonmedical applications to determine the presence of biological organisms on a selected surface, such as a food preparation surface in a restaurant, a slaughterhouse surface or the like.

In accordance with standard specimen collection and test preparation techniques, the biological specimen is normally transferred from the swab tip to a slide or other laboratory apparatus such as a test tube or the like, for contact with the selected reagent or reagents and further analysis. The reagents are typically stored in a vial or other breakable container prior to use. However, it is frequently difficult to ensure transfer of a sufficient specimen quantity from the swab tip to the laboratory slide or test tube to ensure accurate test results. Moreover, in many instances, the collected specimen must be transported to an off-site laboratory for performance of selected assays. Delays between the time of specimen collection and actual test performance can result in partial or complete drying of the specimen, with a corresponding decrease in test reliability. In addition, such conventional handling of a biological specimen in the course of preparing and/or performing an analysis undesirably exposes personnel to direct contact with the collected organism, wherein direct contact with infectious or toxic organisms can be especially undesirable.

In this regard, a variety of swab-type specimen collection and test devices have been proposed in efforts to provide enhanced contact between a specimen and reagents, or to sustain the specimen in an improved manner during transport to a laboratory, while at the same time reducing or minimizing risk of direct personnel contact with the collected specimen.

For example, sampling/test kits are now abundantly available for providing transport or testing of specimens in both a hospital and medical office environment. While these tests may be used in the home of a patient, the kits often involve multiple steps or stages, breakable parts, and in many cases, assembly, making them less desirable for use by the general public. For instance it is not unusual for a kit to include three to four parts such as a swab, a collection dish/tray or chamber, in some cases vials of testing solutions or reagents, and an assay medium such as a test strip. In test devices involving multiple pieces, the various components used to conduct the test must be kept separated in order to avoid possible contamination of either the testing substrate or the reagents/growth media used in the test.

Typically, such kits involve mixing of test solutions, or causing the rupture of a vessel containing the test solution(s), filling a testing dish, tray or vessel with the testing solutions (most often in the form of a small test tube or test chamber), placing the swab in the testing dish, tray or vessel, and either waiting for the results to be observed on a test strip or indicator, or alternatively for a value to be generated. In some instances, such kits also require the removal of the swab, or dipping a testing strip into a testing dish in order to obtain an analysis result. Depending on the type of kit being used, such steps may involve the awkward placement of test solution vials next to the test tray, or the continuous possibility of exposure of biological specimens to the tester.

Further, as many of such test kits utilize a relatively flexible bulbous vessel for dispensing test solutions/reagents directly into a test vessel, upon being squeezed (application of pressure) or upon having an internal component ruptured, such kits present the possibility of inadvertent rupturing of the vessel, or initiation of the test, when such is not desired. Such tests may also present the possibility of injury to the tester as internal components to be ruptured may include glass, reagent containing ampoules.

There is therefore a need for a simplified test device that can be conveniently stored safely in either the home, medical office or other commercial environments, and that requires minimal to no assembly (with few pieces) prior to use. There is a further need for a test device which provides an immediate visual indication readily to a user, of the results of such a test, but which cannot easily be inadvertently initiated or compromised. There is also a further need for a test device which is relatively stable in use, and avoids the need for awkward solution storage vessels or breakable reagent-containing ampoules for operation.

Given the current rise in health care costs and a focus on preventative/preemptive medicine, the members of the general public are performing more preliminary medical testing in their home environments. Such medical testing allows the individual to make basic medical determinations (such as blood sugar levels, cholesterol levels, blood alcohol levels, pregnancy evaluations, and various urinalysis and breath analysis) prior to visiting a physician, offering vast potential savings in both dollars to the consumer, and in time for physicians who can devote more of their time to patients who truly require medical attention. There is therefore a need for diagnostic test devices which are "patient friendly", in that they are easy to operate and relatively contained in their configuration, so as to allow for the efficient identification of possible medical conditions prior to the costly involvement of a medical practitioner. It is to such needs that the current invention is directed.

Finally, in the practice of gastrointestinal and gynecological medicine, numerous more invasive tests are performed in various internal body organs which require the taking of a specimen or sample/biopsy from an internal space. For instance, it is not uncommon for endoscopic procedures to be performed on patients in order to obtain specimens of stomach lining or stomach fluids, so as to detect ulcer-causing bacteria, or in the colon so as to obtain specimens to detect precancerous polyps, related fluids and the like. With such endoscopic procedures, it is not uncommon for the endoscopic devices to include brushes, forceps, snares or baskets to obtain specimens. The specimens from such procedures may then be sent off to a laboratory facility for further analysis. There is therefore a need for an endoscopic swab that could be used as part of a rapid diagnostic device (where appropriate) to detect a medical condition. It is also to such needs that the current invention is directed.

SUMMARY OF THE INVENTION

The present invention addresses problems associated with the prior art. In one embodiment of the invention, a diagnostic test device for detecting the presence of microorganisms includes a cap component. The cap component includes at least one barrel component for receiving a swab. The barrel component includes an inside surface and an outside surface, and defines an interior barrel space. The cap component also includes a results window component for viewing test results from a test strip. The results windows component includes at least one viewing window. The cap component also includes a reagent chamber component between the barrel component and the results window component. The reagent chamber component defines an interior reagent chamber space in spatial communication with the barrel component and the results window component and includes at least one reagent chamber for containing at least one reagent or test solution. The reagent chamber component is rotatably connected to the results window component and rotatable with respect to a core contained in the reagent chamber space. The core includes a test strip. The diagnostic test device may also include a swab component for removable insertion through the barrel component to the reagent chamber component. The swab component may encompass a pre-designed swab to be matingly fit within the barrel component prior to usage. Alternatively, the barrel component may include a rupturable seal over an opening, through which any variety of swabs may be inserted.

The reagent chamber component can be rotated from a pre-use position to a use position, such that when rotated, the reagent chamber moves from a closed position to an open position, thereby delivering reagent contained in the reagent chamber onto the test strip.

In an alternative embodiment of the diagnostic test device, the barrel component includes a first interlocking mechanism on the inside surface, and a pre-designed swab component includes a second interlocking mechanism, such that the first and the second interlocking mechanisms releasably lock with each other, upon insertion of the swab component into the barrel component.

In another alternative embodiment of the diagnostic test device the interlocking mechanism is selected from the group consisting of screw mechanisms, interlocking flange mechanisms, and tab and slot mechanisms.

In another alternative embodiment of the diagnostic test device, the barrel component includes a collar on the inside surface for directing the swab component to the reagent chamber component.

In still another alternative embodiment of the diagnostic test device, the results window component includes at least two windows. In still another alternative embodiment of the diagnostic test device, one of the two windows is a control window.

In still another alternative embodiment of the diagnostic test device, the results window component defines a results window interior space having at least one interior wall inclined toward the results window.

In still another alternative embodiment of the diagnostic test device, the reagent chamber component includes at least two reagent chambers.

In still another alternative embodiment of the diagnostic test device, the core includes structural extensions for directing a reagent to the test strip.

In still another alternative embodiment of the diagnostic test device, the barrel component includes at least one flat side, the results window component includes at least one flat side in alignment with the barrel component flat side, and the reagent chamber component includes at least one flat side, whereby as the reagent chamber component is rotated with respect to the results window component, the reagent chamber component flat side becomes aligned with the barrel and results window component flat sides, as the reagent chamber moves from a closed to an open position.

In still another alternative embodiment of the diagnostic test device, the barrel component includes at least one marking, the results window component includes at least one marking in alignment with the barrel component marking, and the reagent chamber component includes at least one marking, whereby as the reagent chamber component is rotated with respect to the results window component, the reagent chamber component marking becomes aligned with the barrel and results window component markings, as the reagent chamber component moves from a closed to an open position. In still another alternative embodiment of the diagnostic test device, the markings are selected from lines, patterns, symbols, flat and textured surfaces.

In still another alternative embodiment of the diagnostic test device, the test strip is an elongated test strip which is situated within both reagent chamber and results window components.

In still another alternative embodiment of the diagnostic test device, the core is U-shaped. In still another alternative embodiment of the diagnostic test device the core is circular.

In still another alternative embodiment of the diagnostic test device, the swab component includes a handle portion and the handle portion is of such a length that it always protrudes from the barrel component upon insertion into the barrel component.

In still another alternative embodiment of the diagnostic test device, the device is generally tubular/cylindrical in configuration.

In still another alternative embodiment of the diagnostic test device, the U-shaped core defines an interior core space, and the U-shaped core includes an opening into the core space defined by an inner arc in degrees, and further wherein the reagent chambers are defined by an outer arc in degrees, wherein the inner arc is greater in size than the outer arc.

In still another alternative embodiment of the diagnostic test device, the reagent chamber includes side walls, the core has an outer wall, and at least one reagent chamber is formed from the side walls and the outer wall.

In still another alternative embodiment of the diagnostic test device, the reagent chamber includes side walls of a certain height, the barrel component and the results window component include walls of a height greater than or equal to the reagent chamber side walls, and at least one reagent chamber is formed from the reagent chamber side walls, the barrel and results window component walls.

In still another alternative embodiment, a method for detecting the presence of microorganisms includes the steps of: a) providing a diagnostic test device having a cap component comprising at least one barrel component for receiving a swab, the at least one barrel component including an inside surface and an outside surface, and defining an interior barrel space, a results window component for viewing test results from a test strip, the results windows component including at least one viewing window, a reagent chamber component between the at least one barrel component and the results window component; the reagent chamber component defining an interior reagent chamber space in spatial communication with the at least one barrel component and the results window component and including at least one reagent chamber for containing at least one reagent or test solution, the reagent chamber component being rotatably connected to the results window component such that when rotated, the reagent chamber within the reagent chamber component moves from a closed position to an open position, a core situated within the reagent chamber component space, the core being independently rotatable from the reagent chamber component and including a test strip; and a swab component for removable insertion through the barrel component to the reagent chamber component, b) optionally removing the swab component from the device (as the swab may be designed in one embodiment to fit in the device during shipping to keep it sterile and therefore would be removed from the device before it can be used) c) swabbing the swab component onto a selected body cavity, space or environmental location, d) inserting the swab component through the barrel component and into the reagent chamber component (U-shaped core), thereby placing the swab of the swab component adjacent the test strip; e) rotating the reagent chamber component such that the reagent chamber moves from a closed to an open position, thereby delivering the reagent onto the swab and the test strip, and f) viewing the test strip through the window.

BRIEF DESCRIPTION OF THE DRAWINGS

FIG. 2 is a cross sectional view of the diagnostic test device taken along the device length.

FIG. 2A is a cross-sectional view of the diagnostic test device taken along the device width.

FIG. 2B is a cross sectional view of an alternative embodiment of the diagnostic test device taken along the device length.

DETAILED DESCRIPTION OF THE INVENTION

Figure 1:
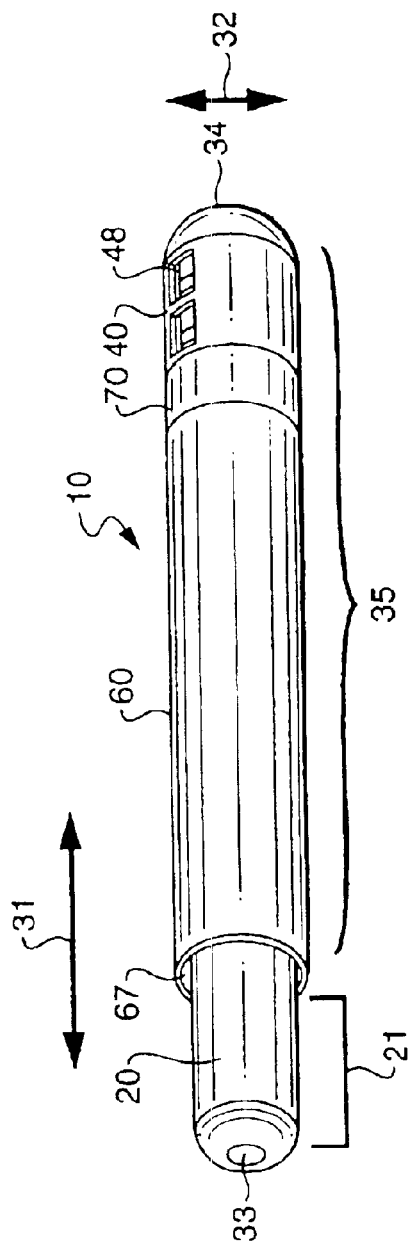
FIG. 1 is a perspective illustration of a diagnostic test device in accordance with the invention.

A diagnostic test device 10 as shown in FIG. 1 and in accordance with the invention, includes a swab component 20 and cap component 35. Such a swab diagnostic device can be used for a variety of test procedures, in both medical office and home/private commercial environments. For instance, such a device may be used for medical testing involving cavity culture testing i.e. throat cultures, rapid strep tests, nasal or vaginal swabs, other body cavity swabs, as well as for the detection of microorganisms in commercial establishments, such as in food service or food preparation industries. The device incorporates all functionality into a two, primary part system for simplicity of use. Essentially the device includes a swab portion and a cap portion that can be used together to form a closed testing environment, and one that reduces the likelihood of tester exposure to microorganisms, spillage of reactant solutions/agents, and the need to perform an awkward series of separate steps and procedures with numerous reagent vials, ampoules or containers. The cap component 35 includes all of the test solutions/reagents, a testing strip and the collections/test dish in one closed location.

Figure 6:
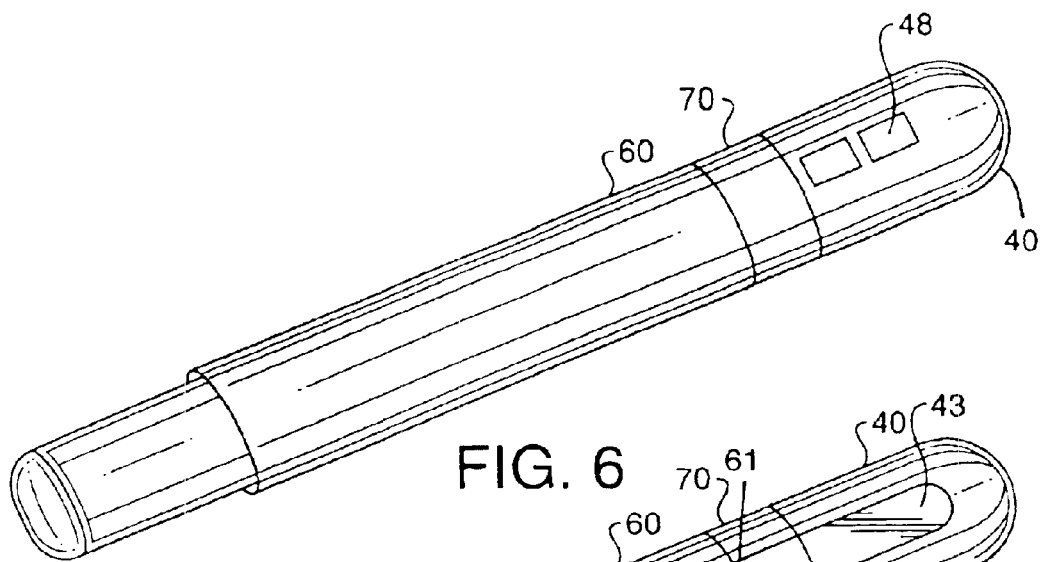
FIG. 6 is a perspective front/top view of the diagnostic test device of FIG. 1 in the "use" position.
Figure 6A:
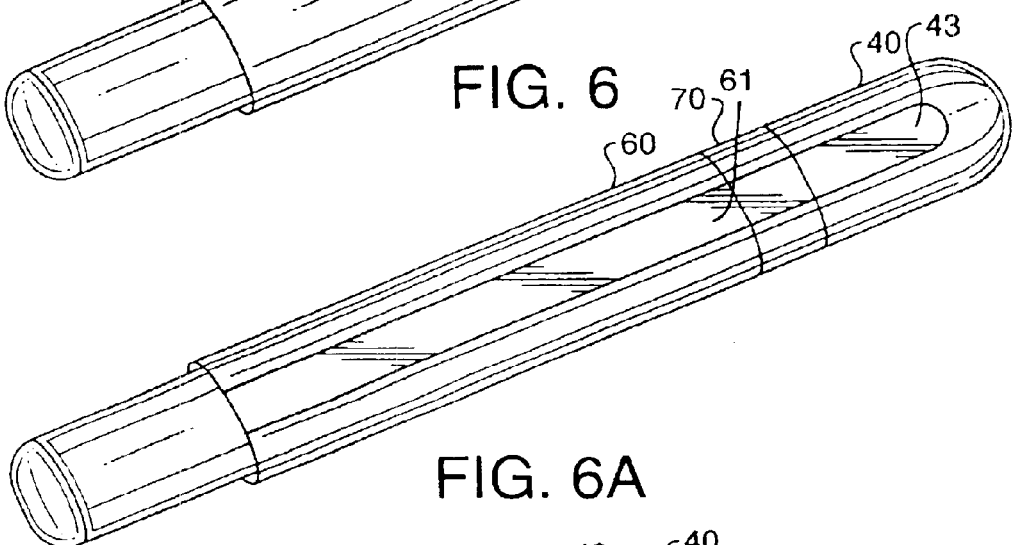
FIG. 6A is a perspective back/bottom view of the diagnostic test device of FIG. 1 in the "use" position.

While the diagnostic test device 10 is shown in a generally cylindrical tubular configuration, it should be appreciated that any of various shapes may be utilized as long as the functionalities of the two primary components are present. For the purposes of efficiency, a tubular housing configuration is illustrated so as to conform to the overall elongated shape of the swab component 20. The overall diagnostic test device 10 has a length dimension (or longitudinal dimension) 31 and a width dimension 32 transverse to the longitudinal dimension. In a first embodiment, the length dimension 31 includes a proximal end (or swab handle end) 33 and a distal end (results window end) 34. It includes a top (front surface) on which the windows are situated, and a bottom (back surface) opposite from the window surface. In one desirable embodiment, the back surface is a flat surface 61 (as seen in FIG. 6A).

Figure 1A:
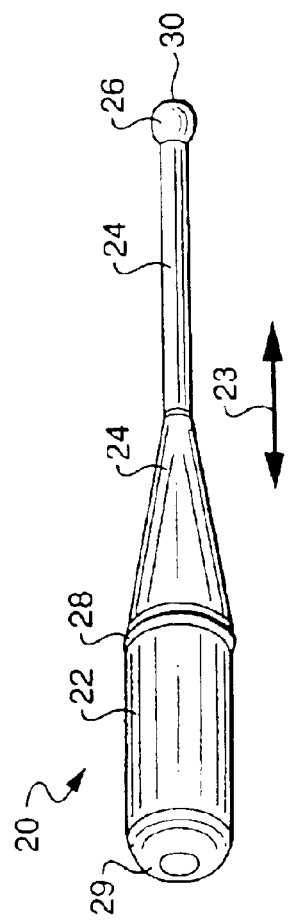
FIG. 1A is a perspective view of the swab component of the diagnostic test device of FIG. 1.

As previously stated, the diagnostic test device can be separated into at least two primary components during use. The first component (swab component) 20 includes the swab itself. The swab component 20 has a length dimension 23 having a proximal handle end 29, as seen in FIG. 1A, and a distal swab end 30. The swab component 20 desirably includes a distinct handle portion 22, which desirably includes along a portion of its circumference, a first interlocking mechanism such as a raised portion or flange 28 which functions as part of a cap component interface/interlocking system, that will lock the cap component 35 (having a second interlocking mechanism) in place around the swab component 20 either prior to use, during use, or after use. Alternatively to a flange 28, the handle portion 22 may include screw-like channels (not shown) along the swab handle circumference, for screwing the swab component 20 into a second interlocking mechanism such as a mated screw portion (not shown) along the inside surface of the cap component 35. In a further alternative embodiment, the handle portion 22 may include a recess (not shown) to receive a mated elevated ridge portion (not shown) on the inside of the cap component 35. It should be understood that in the various embodiments of first and second interlocking mechanisms, either of the mating locking mechanisms may be situated on either of the swab or cap components.

A stem portion 24 of the swab component 20 is immediately connected to the handle portion 22 adjacent the flange 28. At the distal end of the swab component 20, a swab 26 is attached or mounted to the stem portion 24, for collecting specimens for testing. The swab component 20 body is desirably of an injection molded polymer construction, such as a polyethylene or polypropylene. The swab 26 itself, may be constructed of materials typically found in current medical swabs, and may be made from for example, cellulosic materials, synthetic polymeric nonwoven materials, polymeric foams or a combination of such.

Figure 1B:
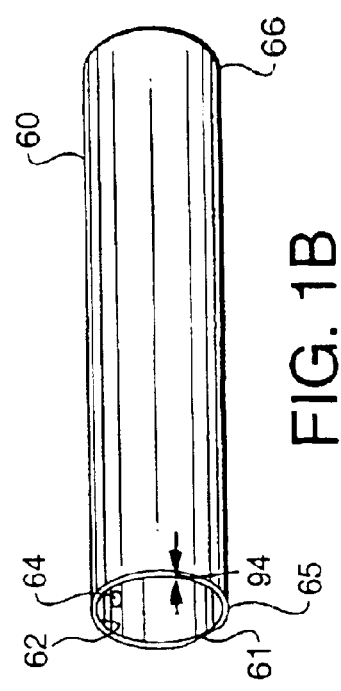
FIG. 1B is a perspective view of the barrel component in the diagnostic test device of FIG. 1.
Figure 1C:
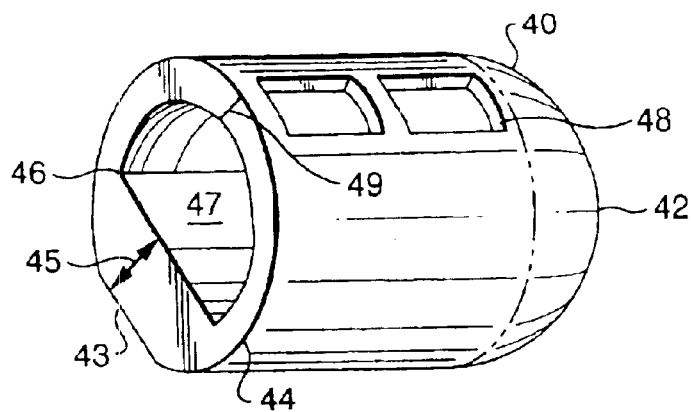
FIG. 1C is a perspective view of the results window component of the cylindrical cap component of the diagnostic test device of FIG. 1.

The cap component 35 is itself desirably constructed from at least three distinct polymeric components, each being desirably made through an injection molded process. The first cap component, or barrel component 60 has an inside 62 and an outside surface, and is designed to enclose/envelop the majority of the swab component 20 within an interior barrel space 100. In particular, the barrel component 60 is designed to enclose (receive) much of the swab handle in the interior barrel space 100, and much of the swab stem 24, but not the swab 26 itself. A portion of the swab handle 22, adjacent the proximal handle end 29 desirably extends beyond 21 the barrel component opening 67 to allow for ease of hand manipulation during use. In this regard, it is desirable that at least between about 0.75–1 inch of the handle 22 extend from the barrel component opening 67 to allow for easy grasp of the swab component 20 with a users thumb and forefinger. The barrel component 60 desirably includes a flat back/bottom surface 61, seen in FIGS. 1B, 2A and 6A. The flat surface 61 is referred to herein as back or bottom since in use, the flat surface may rest on a relatively horizontal surface during testing or storage (such as a tabletop or lab bench) away from the users line of sight. While not required to be resting on such a surface, the diagnostic test device 10 is desirably maintained in a horizontal level position during use (for ease of operation), i.e generally parallel to level ground when in use. This position is not required for operation, but it is desirable, so as to allow the maximum amount of testing solutions/reagents to contact the swab and test strip during use. If a flat back surface 61 is present on the device, the flat surface should be the surface facing the ground/table top, when the device is being used and opposite from the window-side of the device. The remaining barrel component surface is desirably rounded in configuration, as can be seen in the various figure views. It should be appreciated that while such rounded configuration is preferred, any shape configuration is contemplated. For instance, the barrel may be in the shape of a cube or other box form. Having at least one side surface that is flat does offer the benefit that the device will be stable on a flat surface during usage, reducing risk of test solution spillage and subsequent reagent/specimen contamination.

A barrel interlocking component is desirably present along the inside surface 62 of the barrel component 60 for holding the swab component in place either during pre-use storage, or during usage, as will be explained in the following sections. The interlocking component is designed to interlock with a swab component 20 interlocking component as previously stated, upon receiving gentle pressure in a longitudinal direction 64 of the device either toward the distal (result window end) end 34 of the cap component 35, while maintaining the cap component 35 in a non-moving position, by receiving gentle pressure in the longitudinal direction toward the proximal end 33 of the device while maintaining the swab component 20 in a non-moving position, or alternatively, by applying gentle pressure from both the swab and the cap components towards each other (after the swab has been inserted within the barrel component).

The barrel interlocking component is desirably an elevated protuberance or a continuous circumferential ridge/flange 63 (cross section seen in FIG. 2B) on the inside surface 62 of the barrel component 60, over which the swab component flange 28 must pass while the swab component 20 is inserted into the cap component 35. As previously indicated, the interlocking components of both the swab and barrel components may alternatively be screw-type grooves and channels, such that the swab is rotated into and out of position with respect to the barrel component, or alternatively, a mating ridge and recess arrangement. In either instance, the interlocking arrangement is desirably one so as to allow the easy insertion or removal of the swab component 20 into the barrel component 60 with some force (so as to avoid the inadvertent removal of the swab component), but one that would desirably provide a liquid seal once the swab component 20 has been inserted within the cap component 35 and the swab is firmly in its "testing" position. Essentially, the swab and cap interface coaxially and lock together, either by a frictional arrangement, such as in a pen cap, a screw interface, a tab and slot interface, or other suitable sealing system.

The barrel component 60 may itself comprise multiple sub-components in a variety of shapes, so long as it encloses at least a portion of the swab component 20 as previously described. The barrel component 60 desirably includes on its inside surface 62, at the end 66 opposite the opening 65 through which the swab is inserted, an elevated collar structure 71 (as seen in FIG. 2) for directing the swab to the test strip (as will be explained in the following sections). While not required for operation, the presence of an elevated collar structure 71 can achieve the multiple objectives of 1) directing the swab 26 to make contact with the test strip 69 in order to receive the maximum amount of test solution/reagents, 2) locking the swab 26 in place so that it is immoveable, or at least difficult to inadvertently move with respect to the cap component 35, and 3) forcing specimen fluid or tissue samples which may be contained on the swab 26 following swabbing, to be squeezed or directed onto the test strip 69 for later testing. In one embodiment, the elevated collar structure 71 desirably includes a conical depression 95 such that the widest shoulder of the cone is positioned closest to the barrel component end 65. The elevated collar structure 71 is desirable integrally connected to the end 66 of the barrel component 60. The wall thickness (or height) 96 (in the width direction) of the elevated collar structure 71 is designed to serve as a side wall to the reagent chamber 76, as will be later described.

Figure 3:
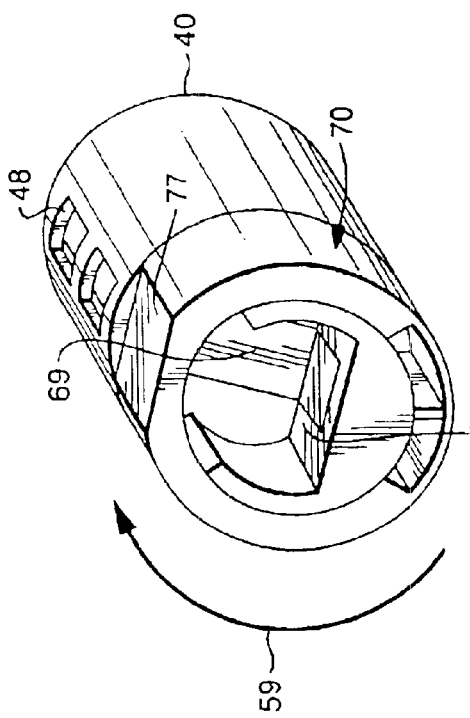
FIG. 3 is a perspective view of the results window and reagent chamber components of the cylindrical cap component of the diagnostic test device of FIG. 1, shown in the "pre-use"/closed storage position.
Figure 4:
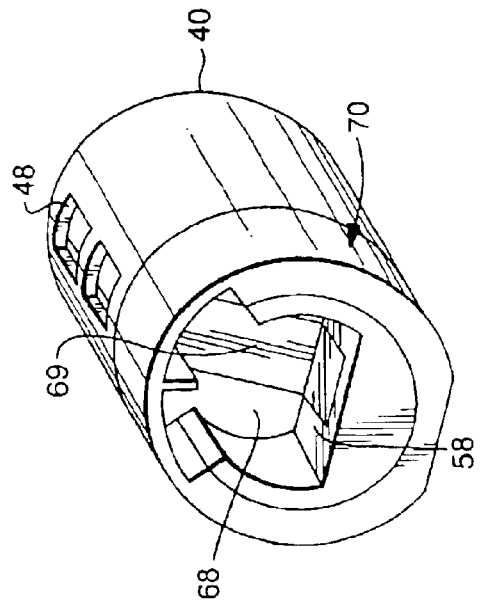
FIG. 4 is a perspective view of the result window and reagent chamber components of the cylindrical cap component of the diagnostic test device of FIG. 1, shown in the "use" /open position.
Figure 5:
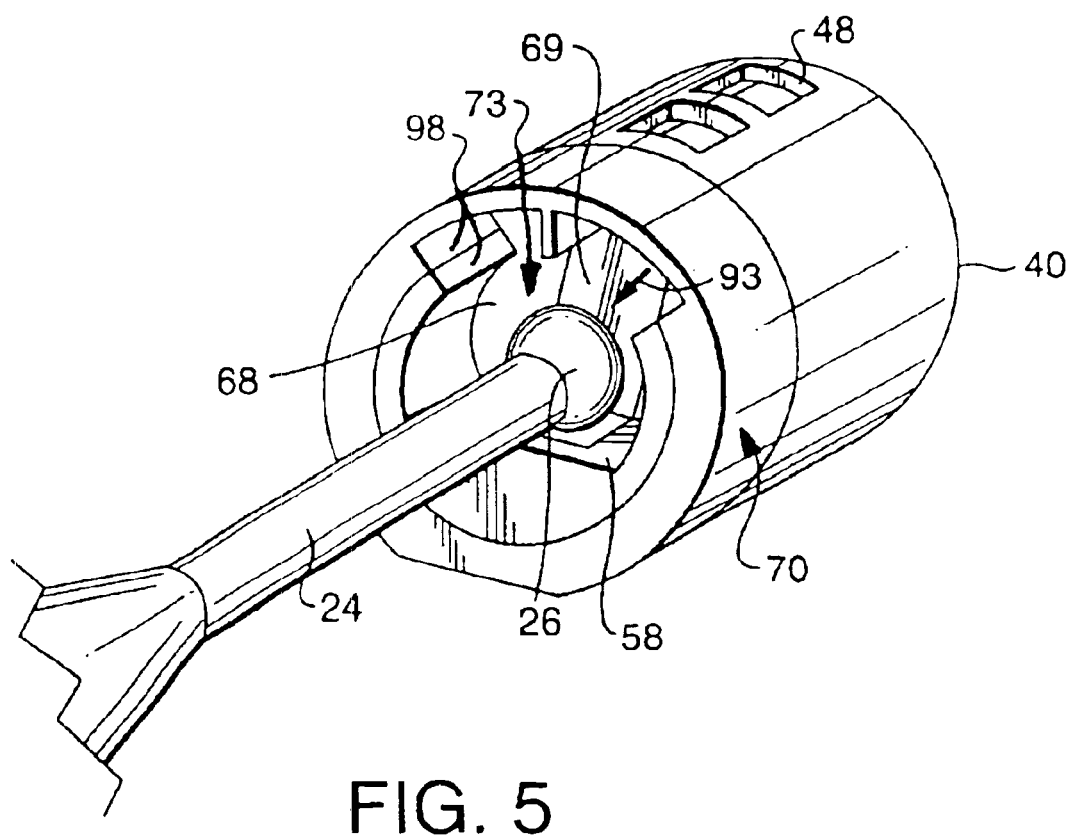
FIG. 5 is a perspective view of the results window and reagent chamber components of the cylindrical cap component of the diagnostic test device of FIG. 1, shown in the "use" position and with a swab inserted in the cap housing.

A results window component 40, as illustrated in FIGS. 1, 1C, 2, 3, 4, and 5, is situated at the distal end 34 of the diagnostic test device 10. The results window component 40 includes at least one viewing window 48 (as the component name suggests), but may include several viewing windows and defines a results window interior space 120. For instance, the results window component 40 may include two windows, one to provide viewing of the test result, the other to provide viewing of a control strip, indicating normal operation of the diagnostic test device 10. An exterior flat outer side surface 43 is desirably present on the results window component 40 as well, and is present on an exterior surface opposite from the viewing window(s) 48. The remaining exterior surface is desirably round, as with the barrel component 60. Desirably, the flat sides 43, 61 of the barrel component 60 and results window component 40 are capable of being aligned, as are the rounded sides. The viewing window(s) 48 of the results window component 40 are desirably made from a clear polymer, but may likewise be made from glass or other clear material in order to provide unhindered viewing of the test strip/results. The viewing window(s) 48 should allow for the observation of either a color change, or the appearance of a symbol/numerical indicator on a test strip 69 which is situated beneath them, and originating from within the testing chamber 73 (as seen in FIG. 5). The interior of the results window component 40 desirably includes an inverted U-shaped opening 46 directly beneath the windows. An elongated test strip 69 is partly situated along the bottom surface 47 of the U-shaped opening. The interior of the result window component 40 may also include a filled polymer section having an angled interior wall 68. The elongated test strip 69 may lie on the angled interior wall 68, as seen in FIG. 5, such that as reagent(s) and organisms react on the test strip 69, the indicator chemistry on the test strip will wick upwards (as part of a lateral flow) such that the test result can be viewed through the result window(s) 48. An angled interior wall 68, while not necessary for operation of the diagnostic test device, also provides the desirable attribute of maintaining either the test specimen or certain reagents within the testing chamber 73, while allowing only specific reagents to wick along the strip to inform a viewer of a specific result. As with the barrel component 60, the results window component 40 may itself be formed from a variety of subsections, and may be of a variety of shapes. For instance, while it is shown generally as cylindrical, it may be box-like in shape (having a square or rectangular cross-section in the width dimension) or prism-like in shape (having a triangular cross-section in the width direction).

Figure 1D:
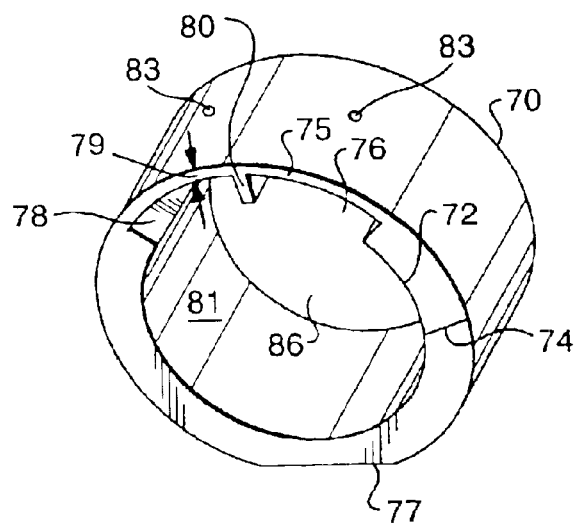
FIG. 1D is a perspective view of the reagent chamber component of the cylindrical ap component of the diagnostic test device of FIG. 1.
Figure 1E:
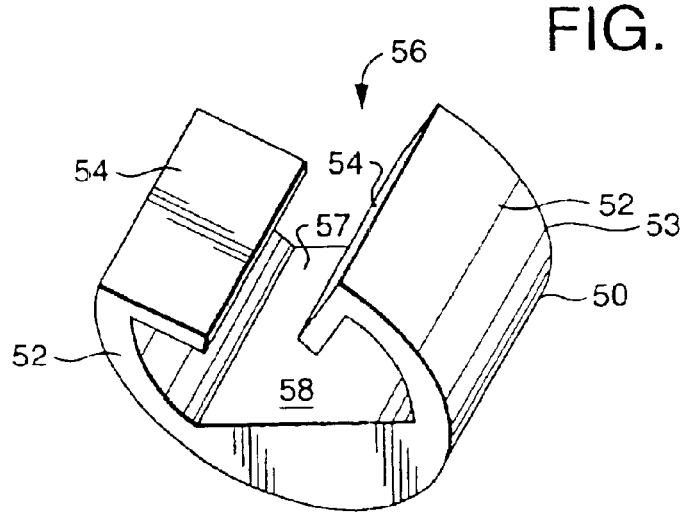
FIG. 1E is a perspective view of the U-shaped core component of the present invention.
Figure 1F:
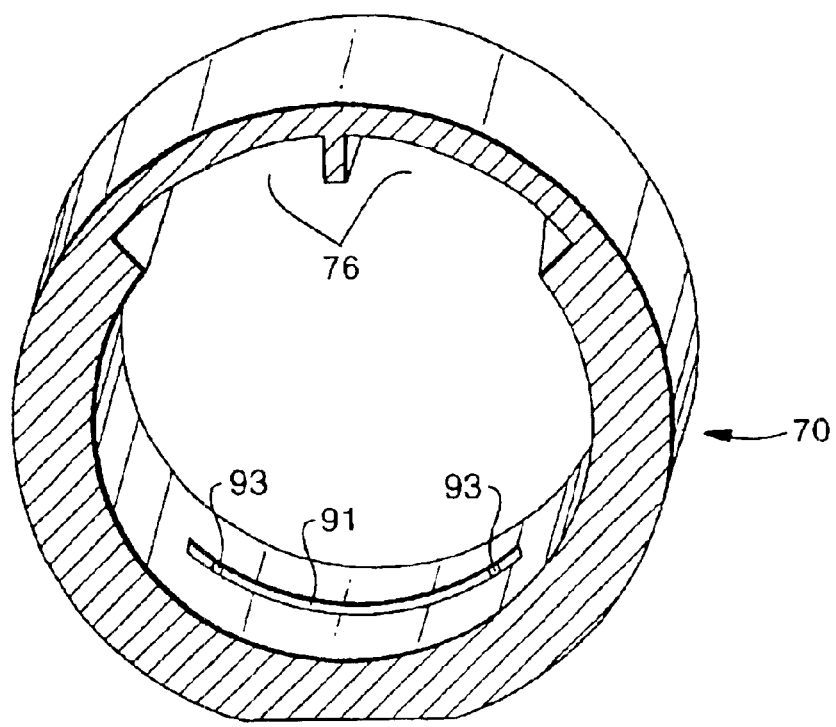
FIG. 1F is a perspective view of an alternative embodiment of the reagent chamber component showing a recess locking mechanism.
Figure 1G:
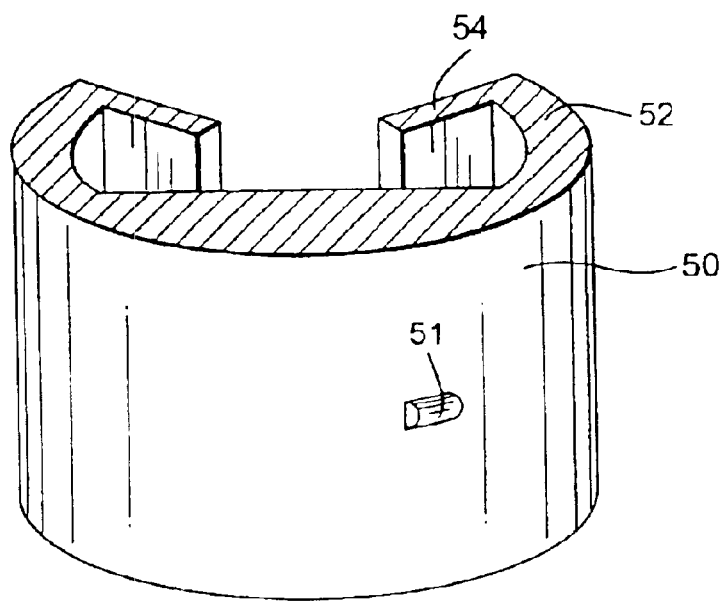
FIG. 1G is a perspective view of an alternative embodiment of the U-shaped core component showing a nib locking mechanism.

As seen in FIGS. 1D, 3, 3A, 4, 4A and 5, the reagent chamber component 70 of the cap component 35 (in the shape of a ring) is immediately adjacent the barrel component 60 and between the barrel component and the results window component 40. As with the barrel chamber component 60, the reagent chamber component 70 desirably includes an outer flat surface 77 on one side surrounded on either side by a round exterior surface. The reagent chamber component defines an interior reagent chamber space 110 in spatial communication with the barrel component 60 (and in particular the interior barrel space 100) and the results window component (interior space). By being in spatial communication, it is meant that a swab 26 or other object (such as the test strip) can either pass between, or is positioned from one cap component to another cap component. The inner walls 72 of the reagent chamber component 70 desirably have an interior wall thickness 74 of a certain dimension around the component circumference, with the exception of the interior wall opposite the interior wall immediately adjacent to the flat exterior surface. The walls help define an interior reagent chamber 76. The thickness (or height) 79 of the interior wall 75 is desirably less than the remaining inner interior walls 72 of the reagent chamber 70. This less thick wall area may be a single area or alternatively, may be sectioned via one or more divider walls 80. If the less thick interior walls 75 are divided into sections, the divider walls 80 separating the sections are desirably of the same height 74 as the thicker inner walls 72. As previously stated, it is desirable that the interior surface wall thickness be thinner (lower height) in the area opposite to that of the flat outer surface, as seen in FIG. 1D. One or more reagent chambers 76 are thus created by the thinner interior walls 75. If there are more than one reagent chambers present, they may be separated by divider walls 80 in a variety of configurations. It should be noted that any number of reagent chambers 76 may be present in the reagent chamber component 70. However, each of the chambers should be situated such that their side walls 78 are directed to the outer flat side 77 of the component if there is one, or alternatively, to the center of the reagent chamber component 70 (center of the ring). The reagent chambers 76 are desirably situated adjacent each other along the ring inner surface, and desirably positioned in a close arc formation along the inner periphery of the ring. As will be discussed in later sections, the size of the arc (outer arc made up of reagent chambers), as measured in degrees, is desirably less than or equal to the size of the arc opening 56 (inner arc) formed in the U-shaped core 50 also to be discussed in a latter section. If the size of the outer arc is greater than the inner arc, then the test diagnostic test device 10 will not efficiently direct test solutions/reagents into the testing chamber 73 during use. Desirably, the size of the outer arc, defining the reagent chambers 76 is less than or equal to 180 degrees. More desirably, the size of the outer arc is between about 90 and 100 degrees. Even more desirably, the size of the outer arc is between about 95 and 99 degrees.

While in the figures the reagent chambers 76 are shown separated by a wall which runs in the longitudinal direction of the device, it is contemplated that such reagent chambers may likewise be situated with separation walls running in the width direction or the direction transverse to the longitudinal direction. In any event, the divider walls and/or side walls i.e. 80 and 78, of the chambers should be directed/angled to the center of the reagent chamber component 70, and if a flat outer side surface 77 is present on the reagent chamber component 70, to the flat outer side surface 77 of the reagent chamber component 70, so as to form a funnel-like opening that narrows towards the center of the reagent chamber component 70. In an alternative embodiment, the reagent chambers 76 may be formed with pre-formed walls on five sides, and with one opening facing the flat side surface/center of the ring. As illustrated, the chambers are shown with two molded walls (78 and 80) from the reagent chamber component 70 and a third wall formed by the relatively thinner interior wall 75 of the reagent chamber component. The remaining chamber walls, which are created during operation of the device, are formed via mechanical rotation of the ring component 70, from the interior walls of the results window component 40 and barrel 60 component.

It should be appreciated that while the majority of the reagent chamber component 70 inner wall 72 is shown as being thicker than the thinner interior wall section 75, this is not necessary for operation of the diagnostic test device 10. For instance, the inner walls 72 need only be thicker at locations immediately surrounding the reagent chamber(s) 76, thereby creating a chamber enclosure.

As previously stated, the reagent chamber component 70, is rotatable with respect to the results window component 40. It may also be rotatable with respect to the barrel component 60, or rotate with the barrel component 60. However, the interior of the reagent chamber component includes a U-shaped core 50 as seen in FIGS. 1E, 3, 3A, 4, 4A, and 5, which is integrally connected with either the results window component 40 or alternatively, the barrel component 60, and desirably does not rotate. In an alternative embodiment, if it is integrally connected with the barrel component 60, either the U-shaped core 50 or the barrel component 60 will be capable of joint mechanical rotation (as one unit) with respect to the reagent chamber component 70, or no mechanical rotation with respect to the reagent chamber component 70. The U-shaped core 50 is of a partial circular configuration in order to allow the reagent chamber component 70 to rotate around it. In this fashion, when the reagent chamber component 70 rotates in a particular direction, it rotates also with respect to the U-shaped core 50 contained therein. The reagent chamber component 70 rotates as a result of any number of rotational technologies known in the art. For instance, it may rotate as a result of a channel/insert between the sides adjacent the barrel and results window components, or it may rotate along screw-like channels such as are found on a multi-component pen.

In an alternative embodiment, it may rotate as a result of a groove and lock mechanism specifically contained between the U-shaped core 50 and the reagent chamber component 70. In this embodiment, the reagent chamber component 70, includes along its lower inside surface 81 a recess 91. The recess 91 includes within its interior portion at least one nib or protuberance 93 to act as a locking mechanism. In a second alternative embodiment two such nibs are present close to each end of the recess 91. A similar nib or protuberance 51 maybe found on the bottom outer wall of the U-shaped core 50. As the device is manufactured, the U-shaped core 50 would be inserted into the reagent chamber component 70 such that the protuberance 51 will be initially situated in the recess 91 or track. In operation, when the U-shaped core 50 is rotated, the nib 51 on the outer surface of the core will be rotated within the recess 91 until it locks in place on either side of the respective nib 93 in the reagent chamber recess/track 91.

The U-shaped core 50 is an insert that fits within the central opening 86 (reagent chamber space) of the reagent chamber component 70, defined by the interior walls/surfaces 72, 81 of the reagent chamber component 70. The U-shaped core 50 includes two arm-like extensions 52 (making up the arms of the circular "U"), which partially envelop an interior space 57 (forming part of a testing chamber 73), and a specimen sample shelf 58. In a first embodiment, the height and dimensions of the arm-like extensions 52 are such that when the core 50 is inserted into the space of the reagent chamber component 70, the arm-like extensions 52 are coaligned with the ledge (created by side walls 78) formed by the thicker interior wall portions 74 of the reagent chamber component 70. This coaligned ledge forms a wall having an extended total thickness/height 98, which directs/helps deliver reagents to the swab 26. This can be clearly seen in FIGS. 4 and 4A. In an alternative embodiment, the arm-like extensions 52 of the U-shaped core 50 include additional structural extensions 54 which are directed towards the center of the U-shaped core 50. Such extensions 54 are designed to further direct test solutions/reagents from the reagent chambers 76 to a test strip 69 when the diagnostic test device 10 is in use. The extensions 54 serve the additional function of providing further enclosure of the swab 26 and exerting additional pressure on the swab 26 so as to squeeze specimen material from the swab 26 onto a test strip 69 lying on the specimen sample shelf 58 (when the swab 26 is in the testing position). The elongated test strip 69 is positioned such that it partially sits on the specimen sample shelf 58 within the testing chamber 73. The test strip 69 sits on the specimen sample shelf 58, but is also positioned such that it lies partly in the testing chamber 73 and partly within the results window component 40, as can be seen in FIGS. 3, 4, and 5. For the purposes of this application, the testing chamber 73 is defined as the open space under the reagent chamber(s) 76 and between the reagent chamber component 70 and the U-shaped core 50, when the reagent chambers(s) 76 are in the in-use open/test position.

The arc opening 56 forms an inner arc of sorts between the arm-like elements 52 of the U-shaped core 50. The size of the inner arc (in degrees of a circle), is desirably equal to or greater than the outer arc size (defined by the reagent chambers 76). If the inner arc size were to be smaller than the outer arc, it is possible that the test solutions/reagents would not fall directly onto the swab 26 or test strip 69 when in use, and would be caught up an interior ledge formed by the outer wall 53 of the core 50.

The U-shaped core 50 is desirably integrally connected with the exterior wall 44 of the results window component 40. In this fashion, the elongated test strip 69 may continue in an uninterrupted path from the upper surface of the specimen sample shelf 58 of the U-shaped core 50 of the reagent chamber component 70, up the angled interior wall 68 of the results window component 40.

As the reagent chamber component 70 (outer portion) is rotatable in a 360 degree fashion, or some degree less than a full circle, the reagent chamber(s) 76 of the reagent chamber component 70, either aligns with the opening 56 of the U-shaped core 50, or alternatively is blocked by some portion of the exterior wall 53 of the U-shaped component 50. As can be seen in FIGS. 3, 3A, 4, and 4A, the position of the reagent chamber component 70 will determine whether materials contained in the reagent chambers 76 will be permitted to fall (via gravity) onto the swab 26 and test strip 69 situated immediately below them when in use (when the testing device in held in a relatively horizontal position parallel with the ground, and with the flat surface facing the ground/away from the user). This is best illustrated in FIGS. 2, 2B and 6 which illustrate the swab component 20 in a testing use position, where all of the flat outer surfaces i.e., 43 and 77 (if present) on each of the barrel component 60, reagent chamber component 70 and results window component 40 are aligned, facing downward. The interior space defined by the reagent chamber component is in spatial communication with both the interior space defined by the barrel component and the interior space defined by the results window component.

In forming the diagnostic test device 10 as described, the height of the interior walls (thickness) on the various components is desirably coordinated so as to avoid leakage of testing solutions/reagents from the various reagent chambers. For instance, the height of the reagent chamber walls, must be less than or equal to the height of the adjacent results window component walls 45 and 49. Likewise, the height of the reagent chamber component walls must also be less than or equal to the height of the barrel component interior walls 94, 96, depending on the presence or absence of the barrel elevated collar structure 71. If the height of the adjacent results windows walls, or barrel component walls (thickness) was less than either of the reagent chamber walls, the reagent or test solutions could leak out from the reagent chambers 76 into the various compartments of either the barrel component 60 or the results window component 40, jeopardizing the accuracy and viability of the diagnostic test device 10.

Further, the frictional contact and/or materials which make up the various subcomponents of the cap component 35, should be such that they encourage the fluid seal of the reagent chambers 76 when the reagent chambers 76 are in a pre-use storage position, and when they are between a pre-use storage position and the testing/use position. Therefore, manufacturing materials such as ultra high modulus polyethylene, polypropylene, syndiotactic polystyrene, cross-linked polyurethane, and polycarbonate may be used to create tight fluid seals, but also provide for the sufficient rotation of the reagent chamber component 70 in operation from a pre-use to a testing/use position. Such materials would not provide undue frictional resistance to the reagent chamber component 70, thereby preventing its rotation with respect to adjacent cap components. Such materials may be injection molded and may be further treated in certain locations to increase hydrophobicity or other repellency around the reagent chambers 76. For instance, Teflon coatings or silicone strips may be situated along the edges of the reagent chambers to encourage retention of solutions within the reagent chambers 76.

Test solutions/reagents may be placed in the reagent chambers 76 either during the diagnostic test device 10 initial manufacture, or following the device manufacture. For instance, the regents may be inserted into the chambers while the device is in a pre-use storage position (when the chambers are entirely enclosed/sealed by six walls) through a port 83 which may be later sealed. Such a port 83 may be in the side exterior wall of the reagent chamber component 70 or other cap component.

In a further alternative embodiment of the diagnostic test device 10, the device may allow for the use of a separately manufactured swab component 20. For instance, the device may include a seal enclosing the opening of the barrel component end 65 (seal not shown) so as to maintain a sterile environment within the device. Such a seal may be manufactured from a polymeric film, or metallic foil for example. During insertion of a separately manufactured swab component 20, the seal may be broken so as to allow the passage of the swab 20 through the barrel component 60 and into the reagent chamber component 70, as previously described.

In still a further alternative embodiment of the diagnostic test device 10, the swab 26 may be part of a separate endoscopic device, such as those endoscopic devices described in U.S. Pat. Nos. 4,700,694 and 5,146,928 and which are each incorporated by reference herein in their entirety. After an endoscopic swab is passed over desired tissue, it may be withdrawn into the endoscope, as with a forceps, snare, basket or brush, and then removed from a patient. The swab 26 may then be inserted into the diagnostic test device 10 as previously described, to provide for an immediate analysis of specific patient conditions.

In one such embodiment, a swab may be positioned with a swab cover at the end of a catheter. The catheter would be designed to be fed through the endoscope as with the previously described biopsy sample collection tools. The cover could be removed and the swab could be fed into the gut or colon for example. The desired tissue could then be swabbed to collect the organism/specimen of interest, and then the swab could be retrieved along with the catheter from the endoscope. For example, such a swab and diagnostic testing device could be utilized to test for the presence of H. Pylori (as part of an ulcer determination).

In performing a diagnostic test utilizing the diagnostic test device 10, multiple steps of testing common to those devices of the prior art, have been reduced to two steps, those being sample collection and testing. Essentially, the mixing of test solutions and exposure of the specimen sample to a test strip has been combined into a two step operation.

Figure 3A:
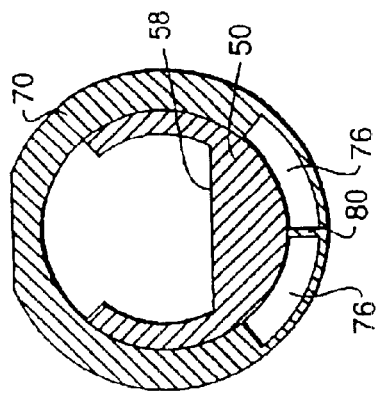
FIG. 3A is a cross sectional view of the cap housing component of FIG. 3.
Figure 4A:
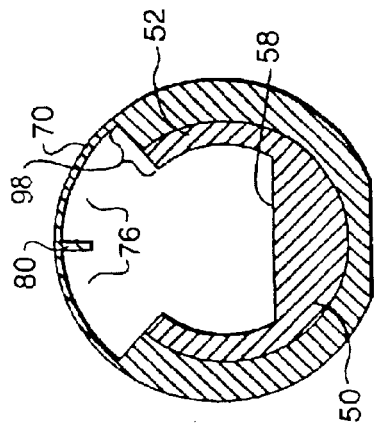
FIG. 4A is a cross sectional view of the cap housing component of FIG. 4.
Figure 6B:
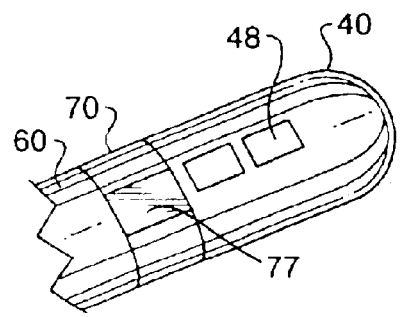
FIG. 6B is a partial perspective top view of the diagnostic test device of FIG. 1 in the "pre-use" storage position.
Figure 6C:
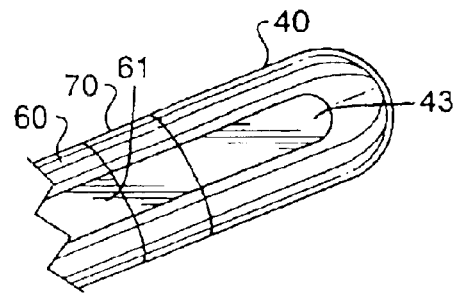
FIG. 6C is a partial perspective back view of the diagnostic test device of FIG. 1 in the "use" position.

In actual operation, the user of the diagnostic test device 10 is desirably provided with the device in a pre-use storage position (as seen in FIGS. 3A and 6B). Essentially, in the pre-use storage configuration, the swab component 20 (if a predesigned swab is contemplated) is held within the cap component 35, the combination of which is desirably held in a hermetically sealed/sterile environment. In this configuration, if the cap components each include a flat outer surface, the flat surfaces of the barrel 60 and results window components 40 are aligned, while the flat surface of the reagent chamber component 70 is aligned with the windows 48 of the results window component 40. Alternatively, the swab component 20 may be stored separately from the cap component 35, each within a hermetically sealed sterile environment, such as a shrink-wrapped container (not shown).

It should be recognized, that in lieu of a flat outer side for alignment purposes, the device may include an alternative marking arrangement, such as a colored line or design element on these outer surfaces. As long as the reagent chamber component 70 marking (i.e. whether coloration, pattern, symbol, textured or flat surface) is not initially aligned with the same marking on the adjacent barrel and results window components, 60 and 40 respectively, the reagent chamber(s) 76 contained within the reagent chamber component 70 will be sealed either by walls within the reagent chamber component 70 itself in combination with the outer surface of the U-shaped core 50, or in conjunction with the three walls within the reagent chamber component 70 and the additional side chamber walls provided by the thicker adjacent interior walls of the barrel component 60 and results window component 40 along with the outer wall of the U-shaped core 50. The reagent chamber(s) 76 will be closed with respect to the testing chamber 73. This configuration keeps the various reagents from mixing, as well as prevents contact of the reagents/test solutions with the elongated test strip 69 prior to use.

The swab component 20 is then either removed from the diagnostic test device cap component 35 and used to swab the environment to be tested, or removed from its own sealed packaging and used to swab. The swab component 20 is then inserted/reinserted into the cylindrical housing cap component 35. The swab component 20 is inserted so that it desirably locks into place by the circumferential ridge/flange (interlocking mechanism) 63, thereby reducing exposure of the user to any potential organisms contained on the swab 26, and preventing the leakage of reagent/test solutions. Upon insertion into the cap component 35, the swab 26 will be directed through the elevated collar structure 71 (if present) to the specimen sample shelf 58. In pushing the swab component 20 into the cap component 35, the swab 26 will move into the cap until it comes to rest upon, or immediately adjacent the test strip 69, which is laying on the specimen sample shelf 58. The rotatable portion of the cap (the rotatable portion of the reagent chamber component 70) is then rotated such that the outer flat side 77 (or marked side) of the reagent chamber component 70 is aligned with the outer flat sides (i.e., 61 and 43) of the adjacent barrel and results window components 60 and 40. As an alternative, the reagent chamber component 70 may include a tab or breaking mechanism in its rotational mechanics such as to require that the rotation stops in the designated position. At this position in the rotation, as represented by the arrow 59 in FIG. 3 and FIG. 4, the rounded sides of the reagent chamber component 70 become aligned with the respective rounded sides of the adjacent cap components. The reagent chambers 76 are essentially moved from a closed to an open position with respect to the testing chamber 73.

The testing solutions/reagents contained in the reagent chambers 76 are dropped via gravity, into the testing chamber 73 and onto the swab 26 and underlying test strip 69. The paths of the reagents are indicated by arrow 93 in FIG. 5. It is therefore desirable that the diagnostic test device 10, be held in a relatively horizontal/level orientation with the viewing windows 48 facing upward. The rotatable reagent chamber component 70 desirably finishes its rotation in a position in which the outer flat side 77 is aligned with the adjacent flat sides of the adjacent cap components, such that the device can desirably sit in a stable position on a horizontal flat surface without the risk of rolling along the surface, or being tipped over.

This directed dropping of reagents (in the testing/use position) causes the reagents to mix on the swab 26 and subsequently onto the underlying elongated test strip 69. The test results generated by the various reagents will then wick/laterally flow up the test strip 69, such that the end result appears in the viewing windows 48. The test results may be the presence of a color change or indicator which appears on the test strip and which can be observed through the viewing windows 48. Alternatively, the result can be a positive or negative indicator or a value/numerical indicator. It should be recognized that one or more viewing windows may be utilized in the results window component 40 as previously described. If a control window is utilized, the user may at this time also view a control reading, indicative of normal operation of the diagnostic test device 10. Following reading of the test results, the entire diagnostic test device 10 can be discarded.

As a result of the sealing ridge or other interlocking mechanism around the inner surface of the barrel component 60 and swab component 20, the cap is desirably liquid tight, thereby preventing release of the reagents or microorganisms contained on the swab 26 during disposal of the device. In this fashion, premeasured reagents/testing solutions are safely employed within the testing device, without risk of contamination of either the user, the surrounding environment or leading to the inadvertent initiation of the test.

Examples of various reagents which may be used to detect and identify microorganisms include one or more of various well known test reagents. Such reagents may be present in either liquid or solid/powder form. The particular test reagent used may be chosen on the basis of the particular type of microorganism species being identified or tissue cells being tested. For instance, commercially available reagents may be used. In one embodiment, a test reagent such as N,N,N,N tetra methyl-p-phenylenediamine dihydrochloride may be used for detecting gonorrhea. Other test reagents such as dimethyl amino-cinnaminaldehyde, beta d galactosidase substrates, gamma glutamylamino peptidase and prolylamine peptidase may also be used for detecting specific species of the genus *Neisseria*. Further test reagents may include, but are not limited to, hippuric acid for detecting Group B *Streptococcus*, L-pyrrolidonyl beta naphthylamide and esculin for detecting Group A *Streptococcus*, and acid or mineral acids, such as citric, acetic, and hydrochloric acid and sodium nitrite, for detecting Group A *Streptococcus* antigen. In still a further embodiment, reagents such as those described in U.S. Pat. Nos. 4,748,113, 4,830,010, and WO 95/11672 (each incorporated by reference herein in their entirety) may be used to detect the presence of urease on a gastrointestinal swab inserted into the diagnostic test device 10. For instance, a urea reagent may be used as a first reactant to generate ammonia on the test strip, in the presence of urease from the swab. A color indicator reagent may also be employed to create a color change on the test strip, based on an increase in pH resulting from the generation of ammonia.

In another example of the diagnostic test device 10, the device may be used to perform a strep organism identification test. In such a test, the back of a patients throat is swabbed in a normal manner and the swab 26 is inserted within the cap component 35, such that the swab 26 comes to rest upon the specimen sample shelf 58, or is situated above/immediately adjacent the test strip 69. The swab component 20 is locked in place via the swab and cap component interlocking system. An elevated collar structure 71 on the barrel component 60 helps direct any strep materials to the test strip 69. The reagent chamber component 70 has within its multiple chambers 76 the reagents citric or acetic acid, and in a second chamber, either sodium nitrite or a similar nitrite compound. The cap component, or more specifically, the reagent chamber rotatable component, is rotated so as to dump the two chambers into a mixed stream over the swab 26. The reagent solution mix is allowed to react with the specimen sample contained on the swab 26 and come into contact with the test strip.

The test strip 69 may comprise a porous paper-based element impregnated at predetermined points with additional agents such as a neutralizing buffer. An example of such a buffer includes trishydroxy-methylaminomethane (TRIS), for reacting with the treated specimen to yield a first color change indicating the presence of strep organism, or a second color change indicating the absence of strep organism. After a short period of time, the user of the diagnostic test device 10 can view the test results through the viewing windows 48. Following the viewing of the results, the user can either bring the diagnostic test device 10 to his/her medical practitioner, or alternatively can dispose of the device, through acceptable medical waste disposal methods.

As will be appreciated by those skilled in the art, changes and variations to the invention are considered to be within the ability of those skilled in the art. Such changes and variations are intended by the inventors to be within the scope of the invention.

What is claimed is:

1. A diagnostic test device for detecting the presence of microorganisms comprising:
   a cap component comprising
      at least one barrel component for receiving a swab, said at least one barrel component including an inside surface and an outside surface, and defining an interior barrel space,
      a results window component for viewing test results from a test strip, said results windows component including at least one viewing window,
      a reagent chamber component between said at least one barrel component and said results window component; said reagent chamber component defining an interior reagent chamber space in spatial communication with said at least one barrel component and said results window component and including at least one reagent chamber for containing at least one reagent or test solution, said reagent chamber component being rotatably connected to said results window component and rotatable with respect to a core contained in said reagent chamber space,
      said core including a test strip; and
      a swab component for removable insertion through said barrel component to said reagent chamber component;
      whereby said reagent chamber component can be rotated from a pre-use position to a use position, such that when rotated said at least one reagent chamber moves from a closed position to an open position, thereby delivering reagent contained in said at least one reagent chamber onto said test strip.

2. The diagnostic test device of claim 1 wherein said barrel component includes a first interlocking mechanism on said inside surface, and said swab component includes a second interlocking mechanism, such that said first and said second interlocking mechanisms releasably lock with each other, upon insertion of said swab component in said barrel component.

3. The diagnostic test device of claim 2 wherein said interlocking mechanisms are selected from the group consisting of screw mechanisms, interlocking flange mechanisms, and tab and slot mechanisms.

4. The diagnostic test device of claim 1 wherein said barrel component includes an elevated collar structure on said inside surface for directing said swab component to said reagent chamber component.

5. The diagnostic test device of claim 1 wherein said results window component includes at least two viewing windows.

6. The diagnostic test device of claim 5 wherein one of said at least two viewing windows is a control viewing window.

7. The diagnostic test device of claim 1 wherein said results window component defines a results window interior space having an angled interior wall angled upward toward said results window.

8. The diagnostic test device of claim 1 wherein said reagent chamber component includes at least two reagent chambers.

9. The diagnostic test device of claim 1 wherein said core includes structural extensions for directing a reagent to said test strip.

10. The diagnostic test device of claim 1, wherein said barrel component includes at least one flat side, said results window component includes at least one flat side in alignment with said barrel component flat side, and said reagent chamber component includes at least one flat side, whereby as said reagent chamber component is rotated with respect to said results window component, said reagent chamber component flat side becomes aligned with said barrel and results window components flat sides, as said reagent chamber component moves from a closed to an open position.

11. The diagnostic test device of claim 1, wherein said barrel component includes at least one marking, said results window component includes at least one marking in alignment with said barrel component marking, and said reagent chamber component includes at least one marking, whereby as said reagent chamber component is rotated with respect to said results window component, said reagent chamber component marking becomes aligned with said barrel and results window component markings, as said reagent chamber moves from a closed to an open position.

12. The diagnostic test device of claim 11, wherein said markings are selected from lines, patterns, symbols, flat and textured surfaces.

13. The diagnostic test device of claim 1, wherein said test strip is an elongated test strip which extends from said reagent chamber component to said results window component.

14. The diagnostic test device of claim 1, wherein said core is U-shaped.

15. The diagnostic test device of claim 1, wherein said core is circular.

16. The diagnostic test device of claim 1, wherein said swab component includes a handle portion and said handle portion is of such a length that it always protrudes from said barrel component upon insertion into said barrel component.

17. The diagnostic test device of claim 1, wherein said diagnostic test device is generally tubular in configuration.

18. The diagnostic test device of claim 15, wherein said U-shaped core defines an interior core space, and said U-shaped core includes an opening into said core space defined by an inner arc in degrees, and further wherein said reagent chambers are defined by an outer arc in degrees, wherein said inner arc is greater in size than said outer arc.

19. The diagnostic test device of claim 1, wherein said reagent chamber component includes side walls, said core has an outer wall, and at least one reagent chamber is formed from said side walls and said outer wall.

20. The diagnostic test device of claim 1, wherein said reagent chamber component includes side walls of a certain height, said barrel component and said results window component include walls of a height greater than or equal to said reagent chamber side walls, and at least one reagent chamber is formed from said reagent chamber component side walls and said barrel and results window component walls.

21. The diagnostic test device of claim 1, wherein said core is integrally connected to said results window component.

22. The diagnostic test device of claim 1, wherein said core is integrally connected to said barrel component.

23. The diagnostic test device of claim 1 wherein said reagent chamber component is integrally connected to said barrel component and is rotatable with said barrel component.

24. A method for detecting the presence of microorganisms comprising the steps of:
   a) providing a diagnostic test device comprising:
      a cap component comprising
         at least one barrel component for receiving a swab, said at least one barrel component including an inside surface and an outside surface, and defining an interior barrel space,
         a results window component for viewing test results from a test strip, said results windows component including at least one viewing window,
         a reagent chamber component between said at least one barrel component and said results window component; said reagent chamber component defining an interior reagent chamber space in spatial communication with said at least one barrel component and said results window component and including at least one reagent chamber for containing at least one reagent or test solution, said reagent chamber component being rotatably connected to said results window component such that when rotated, said reagent chamber within said reagent chamber component moves from a closed position to an open position,
         a core situated within said reagent chamber space, said core being independent from said reagent chamber component and including a test strip; and
         a swab component for removable insertion through said barrel component to said reagent chamber component,
   b) swabbing said swab component onto a selected body cavity or environmental location,
   c) inserting said swab component through said barrel component and into said reagent component, thereby placing the swab on said swab component adjacent said test strip;
   d) rotating said reagent chamber component such that said reagent chamber moves from a closed to an open position, thereby delivering said reagent onto said swab and said test strip,
   e) viewing said test strip through said window.

25. A diagnostic test device for detecting the presence of microorganisms comprising:
   a cap component comprising
      at least one barrel component for receiving a swab, said at least one barrel component including an inside surface and an outside surface, and defining an interior barrel space,
      a results window component for viewing test results from a test strip, said results windows component including at least one viewing window,
      a reagent chamber component between said at least one barrel component and said results window component; said reagent chamber component defining an interior reagent chamber space in spatial communication with said at least one barrel component and said results window component and including at least one reagent chamber for containing at least one reagent or test solution, said reagent chamber component being rotatably connected to said results window component and rotatable with respect to a core contained in said reagent chamber space, said core including a test strip,
      whereby said reagent chamber component can be rotated from a pre-use position to a use position, such that when rotated, said at least one reagent chamber moves from a closed position to an open position, thereby delivering reagent contained in said at least one reagent chamber onto said test strip.

\* \* \* \* \*